(12) United States Patent
Fan et al.

(10) Patent No.: US 12,000,782 B2
(45) Date of Patent: Jun. 4, 2024

(54) ACOUSTIC MODULATED LASERS

(71) Applicant: THE REGENTS OF THE UNIVERSITY OF MICHIGAN, Ann Arbor, MI (US)

(72) Inventors: Xudong Fan, Saline, MI (US); Xueding Wang, Ann Arbor, MI (US); Xuzhou Li, Ann Arbor, MI (US); Yu Qin, Ann Arbor, MI (US); Xiaotian Tan, Ann Arbor, MI (US); Yu-Cheng Chen, Ann Arbor, MI (US); Qiushu Chen, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 380 days.

(21) Appl. No.: 17/421,809

(22) PCT Filed: Jan. 9, 2020

(86) PCT No.: PCT/US2020/012939
§ 371 (c)(1),
(2) Date: Jul. 9, 2021

(87) PCT Pub. No.: WO2020/146637
PCT Pub. Date: Jul. 16, 2020

(65) Prior Publication Data
US 2022/0099573 A1 Mar. 31, 2022

Related U.S. Application Data

(60) Provisional application No. 62/790,759, filed on Jan. 10, 2019.

(51) Int. Cl.
G01N 21/63 (2006.01)
A61B 5/00 (2006.01)
(Continued)

(52) U.S. Cl.
CPC ........... *G01N 21/63* (2013.01); *A61B 5/6876* (2013.01); *H01S 3/08059* (2013.01);
(Continued)

(58) Field of Classification Search
CPC .......................... A61B 5/0071; A61B 5/6876; G01N 21/1717; G01N 21/63; G01N 2201/06113;
(Continued)

(56) References Cited

U.S. PATENT DOCUMENTS 3,297,876 A 1/1967 De Maria
5,963,310 A * 10/1999 Brown ................. G01B 11/162
356/458

(Continued)

FOREIGN PATENT DOCUMENTS

EP 2286874 B1 2/2011
WO WO-2007129682 A1 11/2007

OTHER PUBLICATIONS

Cartwright, J "Why scientists are making human cells emit laser beams"; article [online]. Sep. 10, 2015 [retrieved Mar. 2, 2020}. Retrieved from the internet: <URL: https://horizon-magazine.eu/article/why-scientists-are-making-human-cells-emit-laser-beams.html>; p. 2, paragraph 1.
(Continued)

Primary Examiner — Hina F Ayub
(74) Attorney, Agent, or Firm — Harness, Dickey & Pierce, P.L.C.

(57) ABSTRACT

A laser whose emission is modulated by ultrasound is presented. The laser is usually micron-sized. In response to ultrasound modulation, the laser emission increases and decreases. Such a change in emission can be detected by external optical detectors. This type of laser can be used as a new type of imaging modality, in which laser emission in combination with sound waves or ultrasound waves, is used
(Continued)

for imaging Laser emission has a much narrower spectral linewidth and stronger intensity than fluorescence and therefore is able to achieve higher sensitivity, whereas sound waves are used to provide a better spatial resolution of the laser emission from the laser. In ultrasound modulated laser based imaging, multiple lasers can be placed inside cells or tissues.

15 Claims, 9 Drawing Sheets

(51) Int. Cl.
H01S 3/08 (2023.01)
H01S 3/083 (2006.01)
H01S 3/094 (2006.01)

(52) U.S. Cl.
CPC ........ *H01S 3/083* (2013.01); *H01S 3/094076* (2013.01); *G01N 2201/06113* (2013.01)

(58) Field of Classification Search
CPC ........ G01N 2201/06193; H01S 3/0085; H01S 3/08059; H01S 3/083; H01S 3/094076; H01S 3/09415; H01S 3/169; H01S 3/213
See application file for complete search history.

(56) References Cited

U.S. PATENT DOCUMENTS

| | | | |
|---|---|---|---|
| 9,951,269 B2 | 4/2018 | Yun et al. | |
| 2001/0038651 A1* | 11/2001 | Maleki | H01S 3/0941 372/6 |
| 2005/0257708 A1* | 11/2005 | Sousa | B23K 26/36 101/467 |
| 2006/0290944 A1* | 12/2006 | Arnott | G01N 21/1702 356/519 |
| 2012/0127557 A1* | 5/2012 | Masumura | A61B 5/0095 359/291 |
| 2017/0242280 A1* | 8/2017 | Kryvobok | G02B 27/106 |
| 2019/0296521 A1* | 9/2019 | Yun | H01S 5/1075 |

OTHER PUBLICATIONS

Fikouras, A et al "Non-obstructive intracellular nanolasers"; article [online]. Nov. 16, 2018 [retrieved Mar. 2, 2020}. Retrieved from the internet <URL: https://www.nature.com/articles/s41467-018-07248-0>; see entire document.

Gather, M et al "Single-cell biological lasers"; white paper [online]. Jun. 12, 2011 [retrieved Mar. 2, 2020}. Retrieved from the internet <URL: http://www.intelon.org/publications/GatherNP2011.pdf>; see entire document.

International Search Report and Written Opinion of the International Searching Authority issued in PCT/US2020/012939, dated May 22, 2020, ISA/US (12 pages).

* cited by examiner

ACOUSTIC MODULATED LASERS

CROSS-REFERENCE TO RELATED APPLICATIONS

This application is the U.S. National Phase Application under 35 U.S.C. 371 of International Application No. PCT/US2020/012939 filed on Jan. 9, 2020, which claims the benefit of U.S. Provisional Application No. 62/790,759, filed on Jan. 10, 2019. The entire disclosures of the above applications are incorporated herein by reference.

FIELD

The present disclosure relates to acoustic modulated lasers.

BACKGROUND

Fluorescence imaging is one of the most commonly used technologies in biomedical applications. When applied to biological tissues beyond the surface, the spatial resolution and sensitivity of fluorescence imaging are degraded, which is due mainly to the overwhelming optical scattering in the tissues and also affected by the background autofluorescence. To date, breaking the optical diffusion limit while maintaining the high signal-to-noise ratio (SNR) in fluorescence imaging still remains challenging. On the other hand, ultrasound (US) imaging, owing to the much lower scattering of ultrasound wave in biological tissues, can keep its spatial resolution in deep tissues much better than fluorescence imaging. Therefore, high frequency ultrasound is not only employed for imaging but also adapted to treatment, such as tumor therapy, drug releasing, and nerve stimulation. Recently, ultrasound modulated fluorescence imaging has been explored, aiming to improve fluorescence imaging by leveraging the advantages of ultrasound in spatial resolution and tissue penetration. In this technique, an ultrasound wave at a certain frequency is focused in a scattering medium (such as an optically scattering biological tissue), changing the scattering property in the medium thus modulating the photons transmitting through the modulated area. When building an image from the medium, only the modulated photons carrying the ultrasound frequency will be used while the non-modulated photons will be filtered out. Although holding the potential to improve the spatial resolution of optical imaging, this method suffers from a low signal-to-noise ratio (SNR) resulting from the limited modulation depth, which is defined as the modulated photons over the total photons detected. In an alternative method of ultrasound modulated optical imaging, microbubbles labeled with fluorophores and quenchers were used. The volume of a microbubble is changed under the ultrasound pressure wave, leading to the emergence of fluorescence due to the increased distance between the fluorophores and the quenchers. Since this method still relies on the detection of fluorescence, which is weak in intensity and broad in spectrum, its SNR and spatial resolution are still limited.

In contrast to fluorescence-based detection and imaging, laser emission-based detection and imaging has recently emerged as a novel technology in biomedical research. Compared to fluorescence, laser emission has strong intensity and extremely narrow linewidth, which leads to significantly improved SNR, imaging contrast, and sensitivity in sensing biological changes.

In this disclosure, ultrasound modulated micro-sized lasers are explored. Such lasers can leverage the deep tissue penetration and the high resolution of ultrasound imaging and the high SNR, imaging contrast, and sensitivity of laser emission.

This section provides background information related to the present disclosure which is not necessarily prior art.

SUMMARY

This section provides a general summary of the disclosure, and is not a comprehensive disclosure of its full scope or all of its features.

In one aspect, an imaging system is presented. The imaging system includes: a laser, a modulating source, an optical detector and a controller. The laser outputs a laser beam and is configured such that its largest dimension is less than a millimeter. The modulating source generates acoustic radiation and is configured to modulate the laser beam with the acoustic radiation. The optical detector is configured to detect the modulated laser beam from the laser; and the controller interfaced with the modulating source and the optical detector.

The laser may take different forms including a microsphere laser, a ring resonator laser, a distributed feedback laser, a nanowire laser, a plasmonic laser or a photonic crystal laser. In one embodiment, the imaging system employs one or more microsphere lasers comprised of oil doped with dyes. In some embodiments, the laser is embedded into at least one of a cell, tissue or blood vessel of a subject.

In one embodiment, the modulating source is configured to modulate amplitude of the laser beam. The modulating source may also be configured to focus the acoustic radiation and to report position of the focused acoustic radiation to the controller.

In another aspect, a method is presented for tracking migration of cells in a living subject. The method includes: injecting at least one laser into a given cell of the living subject; modulating a laser beam emitted from the laser using acoustic radiation; and detecting the modulated laser beam, thereby determining position of the given cell in the living subject.

In yet another aspect, a method is presented for tracking blood flow in a circulatory system of a living subject. The method includes: injecting at least one laser into a blood vessel of the circulatory system of the living subject; modulating a laser beam emitted from the laser using acoustic radiation; and detecting the modulated laser beam, thereby determining position of the laser in the circulatory system of the living subject.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

wavelength=473 nm); whereas, a focused ultrasound beam was transmitted through the coupling medium.

Figure 2A:
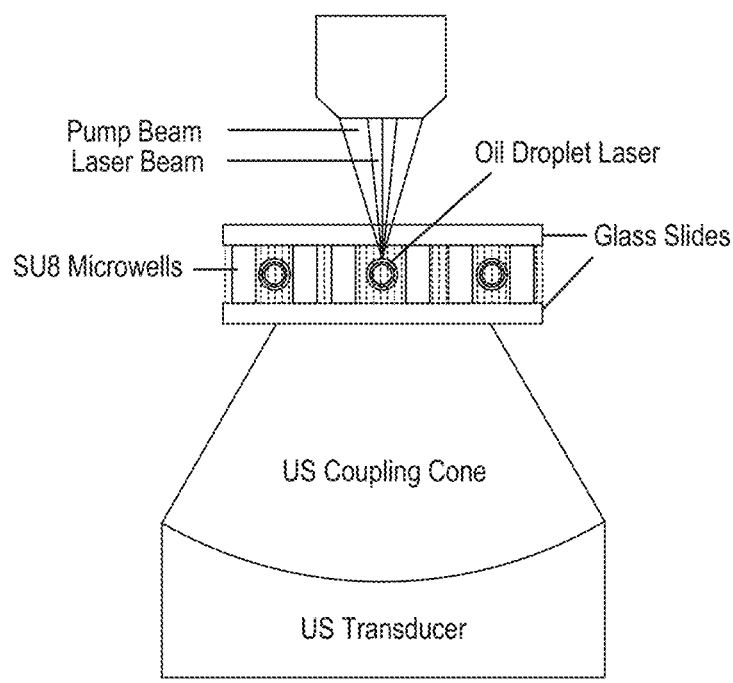
FIG. 2A is a schematic of the optical and ultrasound experimental setup, in which the oil droplets were trapped inside microwells. The oil droplets doped with BODIPY were excited by a pulsed diode laser (pulse width=2 ns.
Figure 2B:
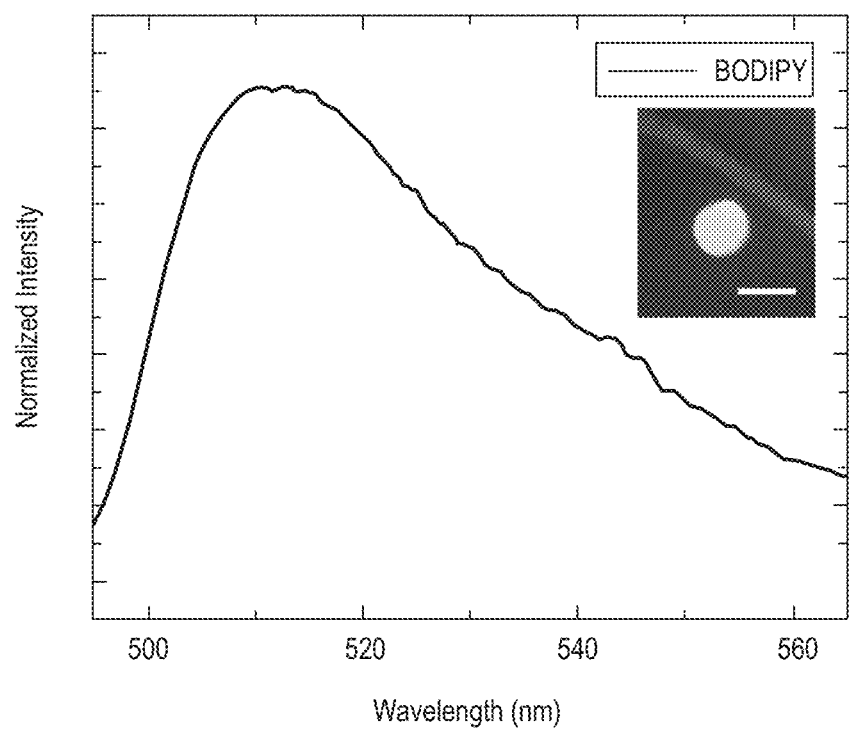

FIG. 2B is a graph showing a fluorescence spectrum of a single oil droplet in the microwell below the lasing threshold, where the inset is a CCD image of the droplet.

Figure 3A:
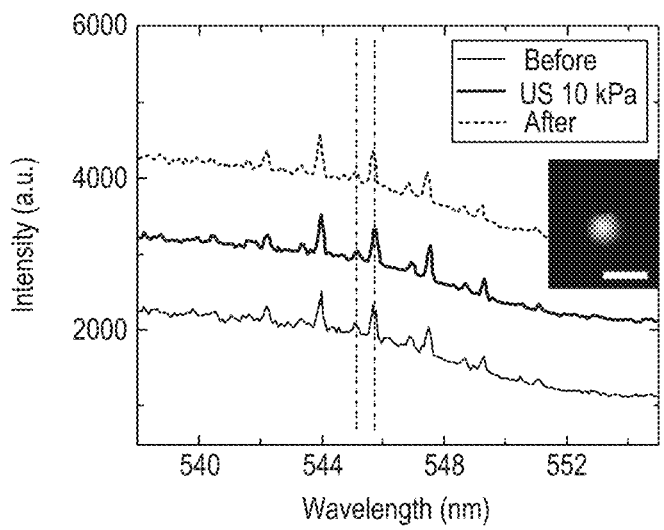
Figure 3B:
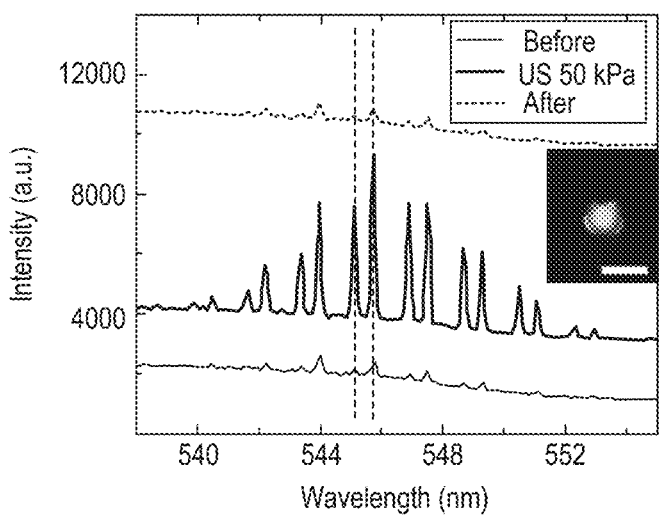
Figure 3C:
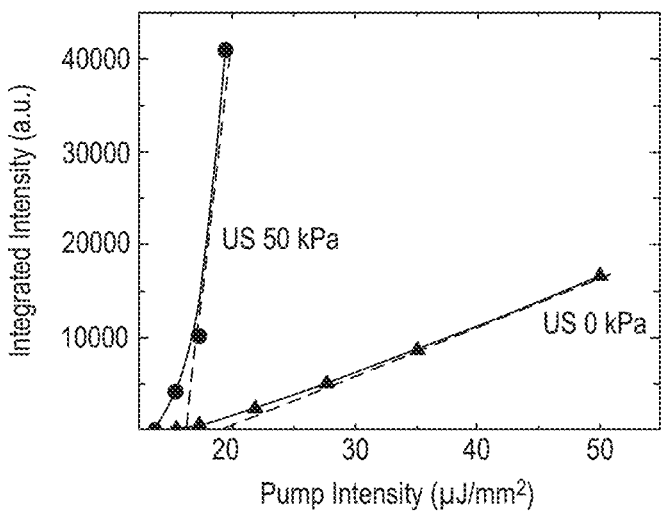

FIGS. 3A-3C are graphs showing lasing enhancement with exposure to ultrasound. In FIG. 3A, lasing spectra of the oil droplet laser is shown before, during, and after applying ultrasound pressure of 10 kPa, where the inset is a CCD image of the droplet laser without ultrasound. In FIG. 3B, lasing spectra of the oil droplet laser is shown before, during, and after applying ultrasound pressure of 50 kPa, where the inset is a CCD image of the droplet laser with ultrasound. All curves in FIGS. 3A and 3B were obtained under the same pump energy density of 35 $\mu J/mm^2$. Curves in FIGS. 3A and 3B are vertically shifted for clarity. Dashed lines in FIGS. 3A and 3B are guides for better observation of the lasing wavelength. In FIG. 3C, laser output integrated over the spectral range of 540-560 nm as a function of the pump energy density, where the measurements with ultrasound (50 kPa) and without ultrasound (0 kPa) exposure are compared. The dashed lines are the linear fit above the respective lasing thresholds under ultrasound pressure of 50 kPa and 0 kPa. With the exposure to 50 kPa ultrasound, the lasing threshold is reduced from 19 $\mu J/mm^2$ to 11 $\mu J/mm^2$.

Figure 4A:
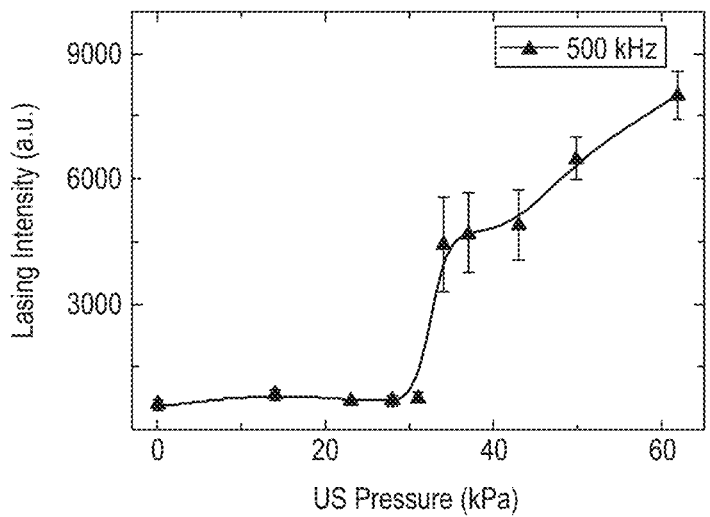
Figure 4B:
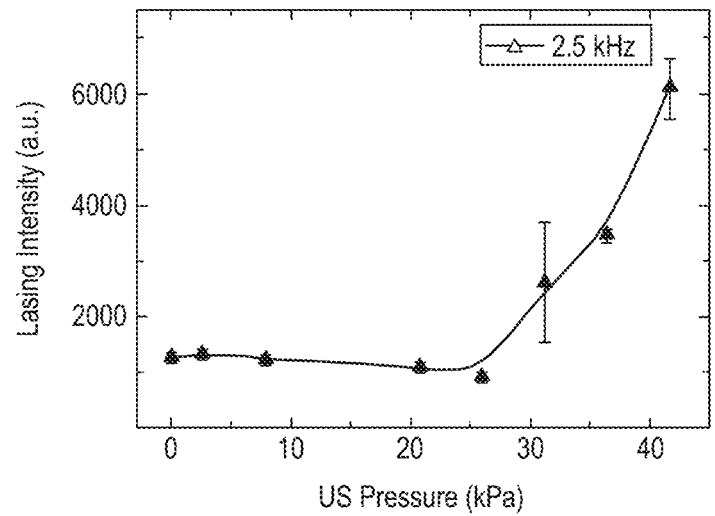
Figure 4C:
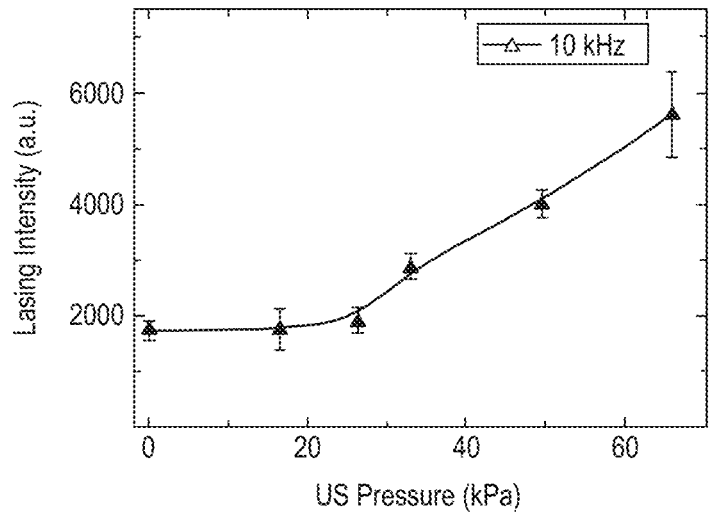

FIGS. 4A-4C are graphs showing lasing intensity as a function of ultrasound pressure for ultrasound frequency of 500 kHz, 2.5 MHz, and 10 MHz, respectively. All lasing intensities were extracted from the spectra collected under a pump energy density of 40 $\mu J/mm^2$ and an integration time of 1 s. Error bars were obtained with five measurements.

Figure 5A:
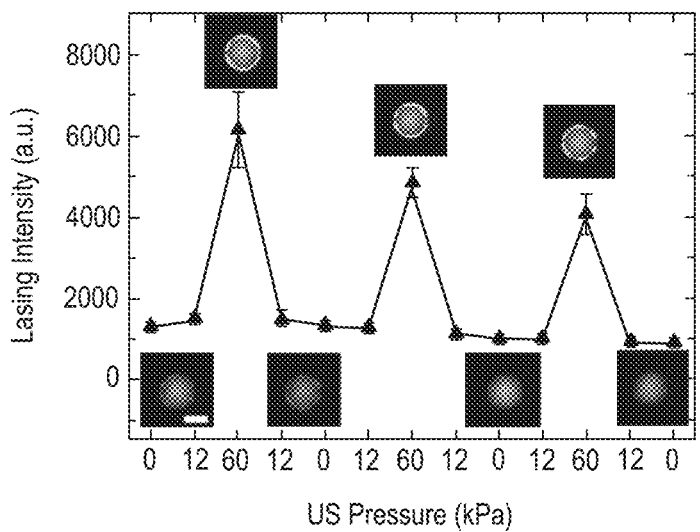
Figure 5B:
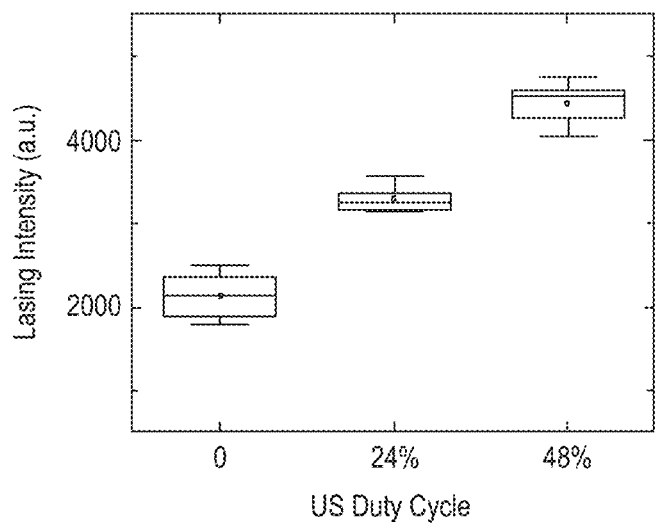
Figure 5C:
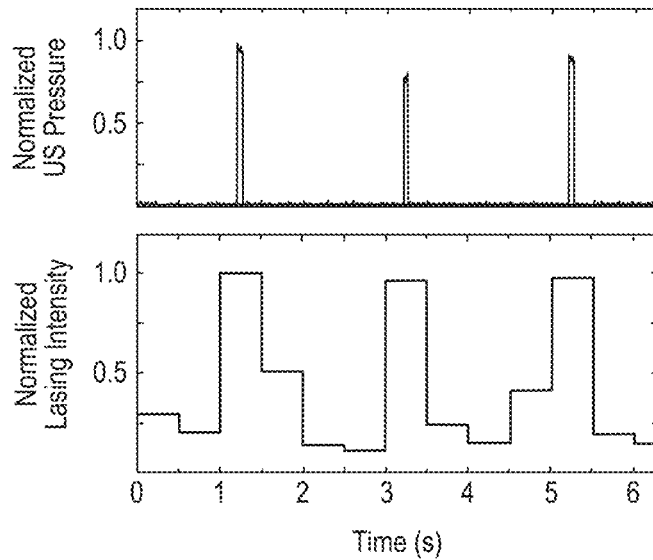

FIGS. 5A-5C are graphs showing modulation of a laser by ultrasound. In FIG. 5A, observation of laser intensities over multiple 500 kHz ultrasound pressure cycles (→12 kPa→60 kPa→12 kPa→0) are shown. The overall downward trend of lasing intensity was caused by the photobleaching effect. Error bars were obtained with five measurements. In FIG. 5B, lasing intensity is modulated by the duty cycle of 500 kHz ultrasound at 50 kPa. When the ultrasound duty cycle increases, lasing output increases accordingly. All lasing intensities in FIGS. 5A and 5B were extracted from the spectra collected under a pump energy density of 40 $\mu J/mm^2$ and an integration time of 1 s. In FIG. 5C, lasing emission enhanced by short ultrasound bursts (500 kHz, 60 kPa, 60 ms burst duration, 0.5 Hz repetition frequency), where the top curve is ultrasound driving signal acquired by an oscilloscope and the bottom curve is extracted from a series of spectra under a pump energy density of 40 $\mu J/mm^2$ and an integration time of 0.5 s. The repetition rate of the pump is 20 Hz, which ensures that there is at least one pump during the ultrasound burst.

Figure 6A:
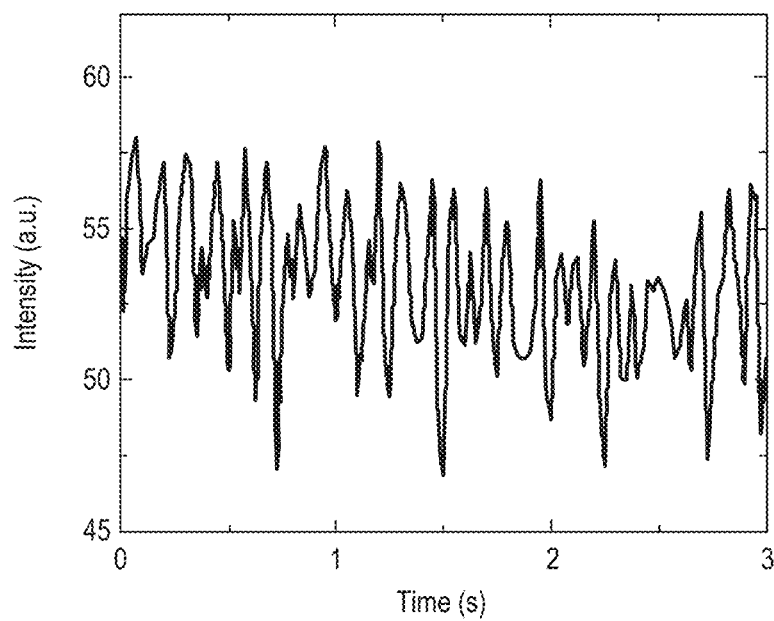
Figure 6B:
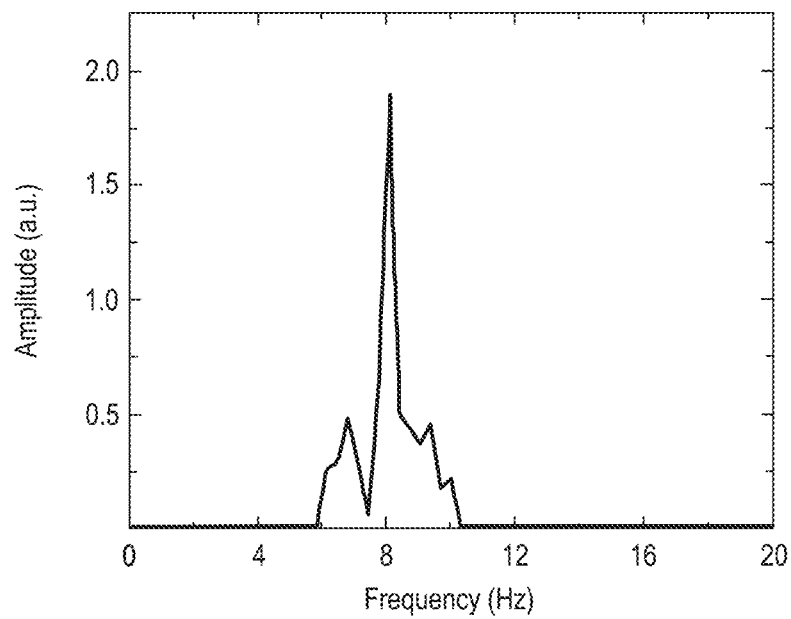
Figure 6C:
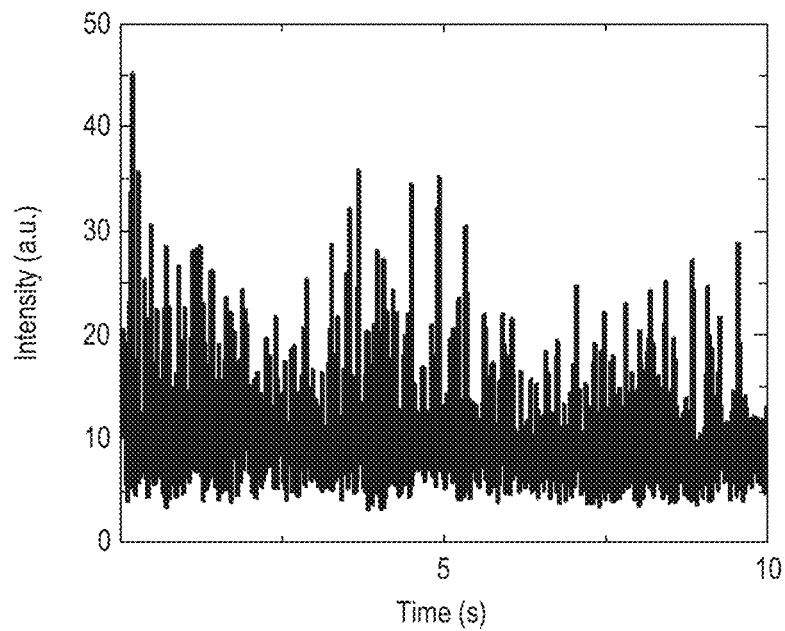
Figure 6D:
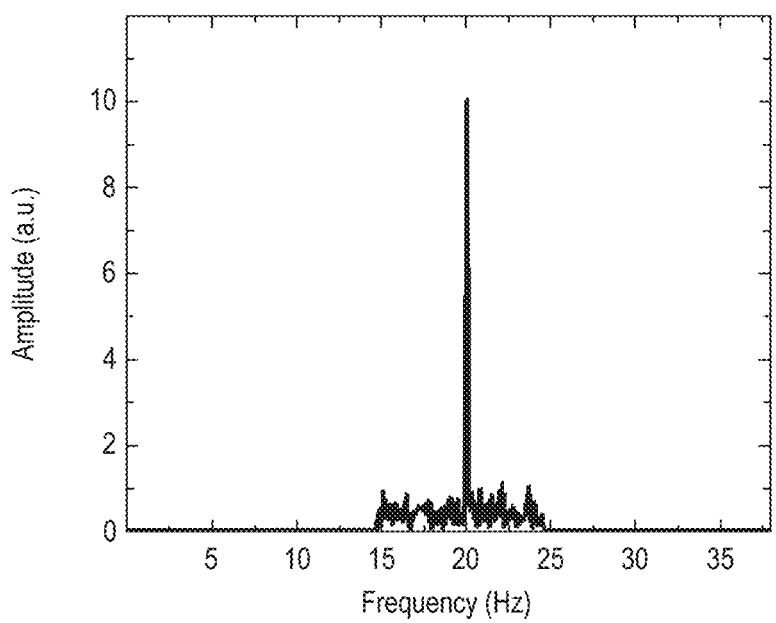

FIGS. 6A-6D are graphs showing lasing emission modulated temporally by ultrasound. In FIG. 6A, lasing intensity is recorded in the time domain modulated by ultrasound bursts (500 kHz, 60 kPa, 30 ms burst duration, 8 Hz repetition frequency). The lasing intensity under a pump energy density of 50 $\mu J/mm^2$ with a pulse repetition rate of 40 Hz was recorded from a CCD with 40 fps. In FIG. 6B, frequency spectrum when applying FFT to the lasing intensity in FIG. 6A with a bandpass filter (6-8 Hz). A peak at the 8-Hz modulation frequency can be noted. In FIG. 6C, lasing intensity recorded in the time domain modulated by ultrasound bursts (500 kHz, 60 kPa, 15 ms burst duration, 20 Hz repetition frequency). The lasing intensity under a pump energy density of 50 $\mu J/mm^2$ with a pulse repetition rate of 80 Hz was recorded from a CCD with 80 fps. In FIG. 6D, frequency spectrum when applying FFT to the lasing intensity in FIG. 6C with a bandpass filter (15-25 Hz). There is a notable 20 Hz modulated component in the spectrum.

Figure 7A:
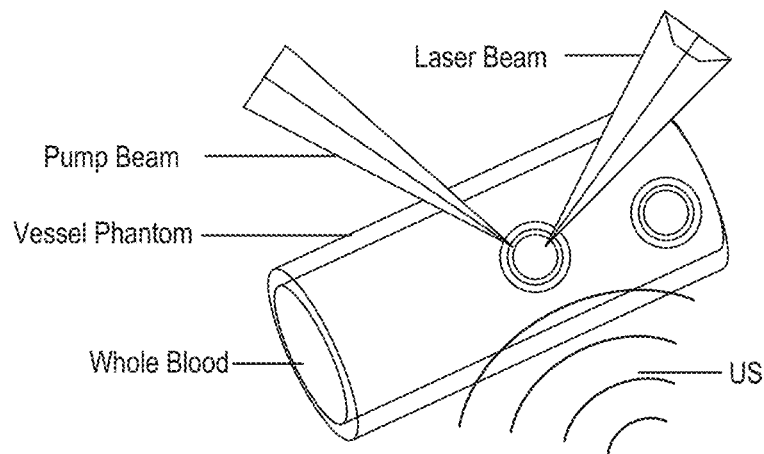

FIG. 7A is a diagram of an experimental setup.

Figure 7B:
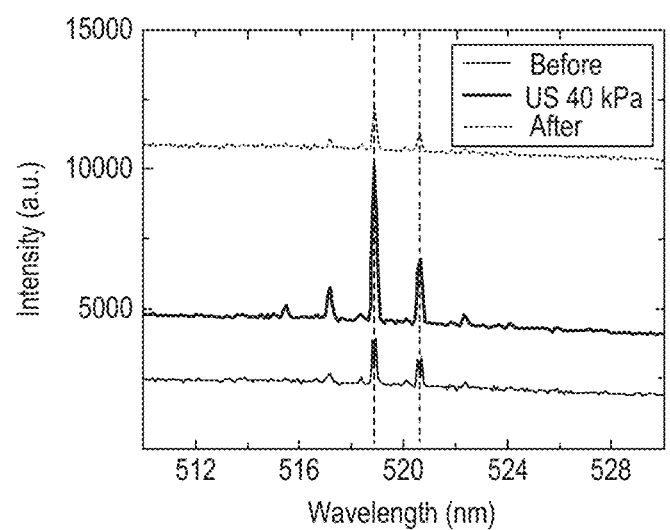
Figure 7C:
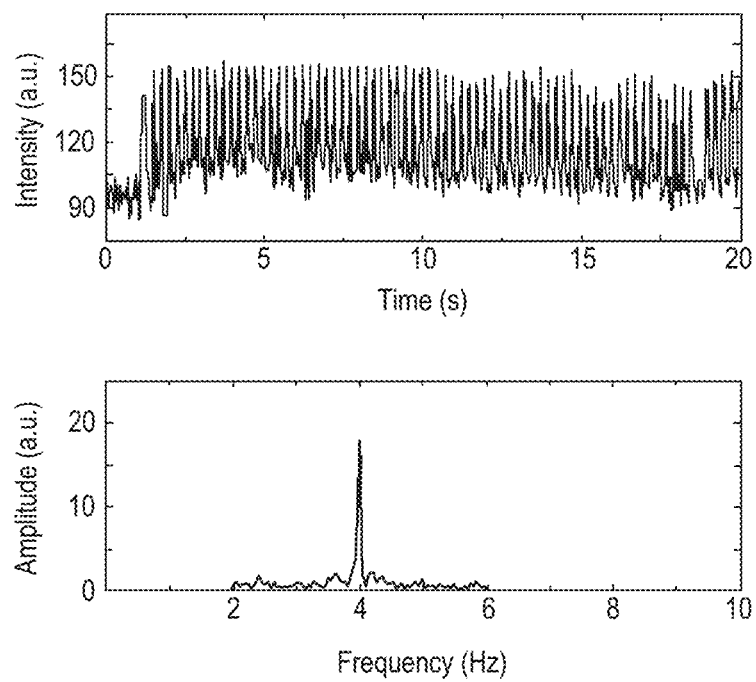

FIGS. 7B and 7C are graphs showing lasing spectra of an oil droplet laser mixed with human whole blood and loaded into a capillary before, during, and after applying ultrasound pressure (40 kPa at 500 kHz). All curves were obtained under the same pump energy density of 50 $\mu J/mm^2$ with a pulse repetition rate of 20 Hz. Curves are vertically shifted for clarity. In FIG. 7C (top), lasing intensity collected from the whole blood in the time domain with ultrasound bursts (500 kHz, 60 kPa, 60 ms burst duration, 4 Hz repetition frequency). The lasing intensity was recorded from a CCD with 20 fps under a pump energy density of 70 $\mu J/mm^2$ with a pulse repetition rate of 20 Hz. In FIG. 7C (bottom), corresponding frequency spectrum of the lasing intensity processed with a bandpass FFT filter (2-6 Hz). There is a notable 4 Hz component in the spectrum.

Corresponding reference numerals indicate corresponding parts throughout the several views of the drawings.

DETAILED DESCRIPTION

Example embodiments will now be described more fully with reference to the accompanying drawings.

Figure 1:
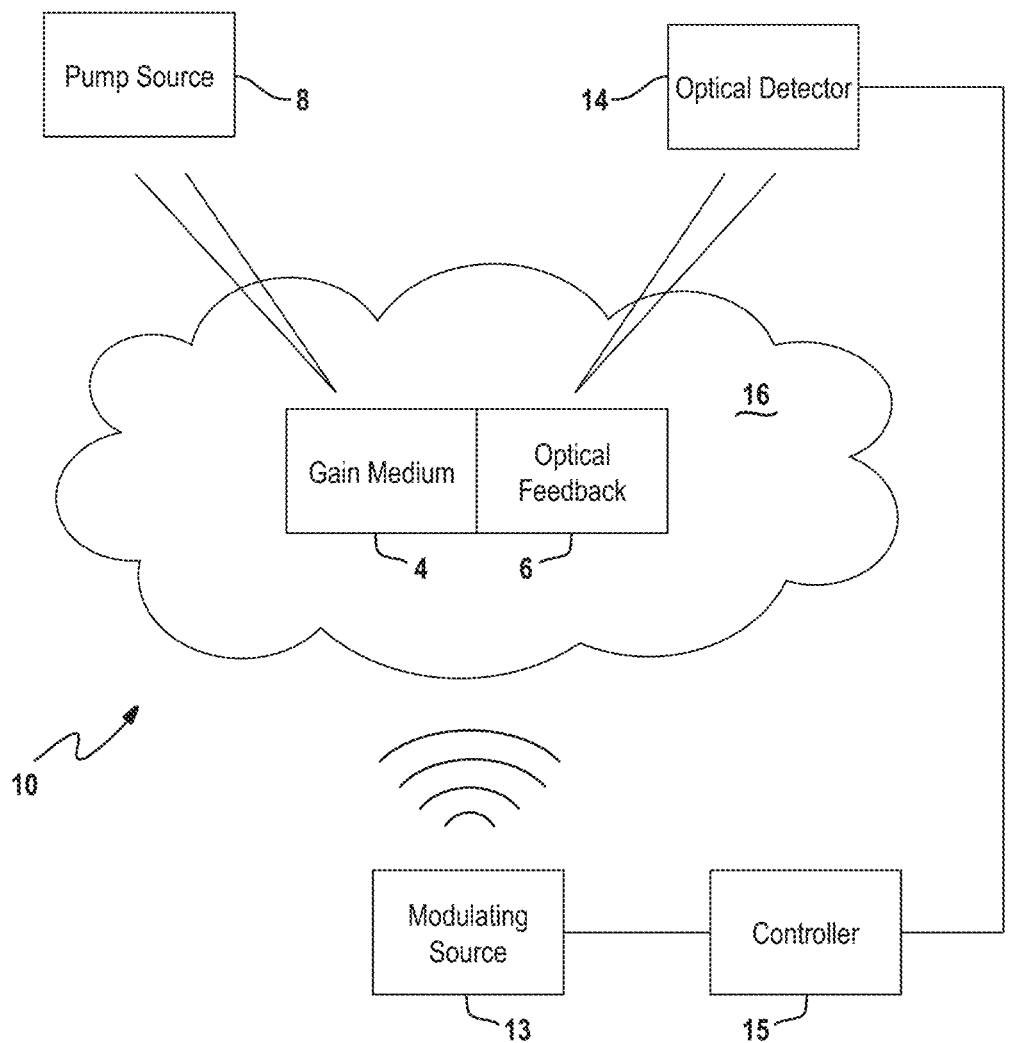
FIG. 1 is a diagram depicting an imaging system which employs acoustic modulated lasers.

FIG. 1 depicts an imaging system 10 which employs acoustic modulated lasers. The imaging system 10 is comprised of a laser 12, a modulating source 13, an optical detector 14, and a controller 15. Each of these components are further described below.

The laser 12 generates and outputs a laser beam. More specifically, the laser 12 includes a gain medium 4, an optical feedback component 6 and an external pumping source 8. In some embodiments, at least a portion of the laser 12 (i.e., the gain medium and the optical feedback component) is embedded into a biological sample 16. The biological sample may include but is not limited to a cell, tissue or a blood vessel of the subject. In these embodiments, the largest dimension of the embedded portions of the laser is less than a millimeter.

In an example embodiment, microsphere lasers may be used in the imaging system. Different types of microsphere lasers include oil droplet doped with dyes, quantum dots or some other types of gain media, or microspheres made of polymer, silica, silicon or combinations thereof and doped with dyes, quantum dots or some other types of gain media. Other types of lasers which meet the size criteria include ring resonator lasers, distributed feedback lasers, nanowire lasers, plasmonic lasers or photonic crystal lasers although other types of lasers are contemplated as well.

The modulating source 13 operates to generate acoustic radiation and is configured to modulate the laser beam with the acoustic radiation. In one example, the modulating source 13 is configured to modulate amplitude of the laser beam, for example by directing a square wave towards the biological sample. The square wave is formed by toggling the intensity of the acoustic radiation between a low value and a high value. In the context of this disclosure, acoustic radiation is intended to include both sound waves (i.e., with frequencies in the range of 20 to 20,000 Hertz) and ultrasound waves (i.e., with frequencies in the range of 20,000 Hertz to several gigahertz). In some embodiments, the modulating source 13 is configured to focus the acoustic radiation on the order of microns and to report position of the focused acoustic radiation to the controller.

The optical detector 14 is configured to detect the modulated laser beam from the laser 12. Example implementations for the optical detector include but are not limited to a charge-coupled device (CCD), a CMOS, a photomultiplier tube or a spectrometer.

The controller 15 is interfaced with the modulating source 13 and the optical detector 14. In an exemplary embodiment, the controller 15 is implemented as a microcontroller. It should be understood that the logic for the control of imaging system by controller 15 can be implemented in hardware logic, software logic, or a combination of hardware and software logic. In this regard, controller 15 can be or can include any of a digital signal processor (DSP), microprocessor, microcontroller, or other programmable device which are programmed with software implementing the above described methods. It should be understood that alternatively the controller is or includes other logic devices, such as a Field Programmable Gate Array (FPGA), a complex programmable logic device (CPLD), or application specific integrated circuit (ASIC). When it is stated that controller 15 performs a function or is configured to perform a function, it should be understood that controller 15 is configured to do so with appropriate logic (such as in software, logic devices, or a combination thereof).

During operation, the modulating source 13, the optical detector 14 and the controller 15 cooperate to detect the modulated laser beam from the laser. For example, the modulating source 13 scans the focal point through the biological sample. When aligned, the laser beam from the laser is modulated by the acoustic radiation from the modulating source. The modulated laser beam is in turn detected by the controller and the positon of the laser beam is known based on the position of the focal point reported by the modulating source 13 to the controller 15. In some embodiments, multiple laser may be embedded into the biological sample. In the case, the laser is amplitude modulated at a constant frequency, a bandpass filter may be used to detect the modulated laser beam. It is readily understood that the filter may be implemented in hardware, software, or both.

FIG. 2 depicts an experimental setup for an example embodiment of the imaging system 10. In the example embodiment, a droplet laser includes oil doped with fluorescence dyes, such as BODIPY. BODIPY used in this example was purchased from ThermoFisher (Catalog #D3921). Detergent and dichloromethane were purchased from Sigma-Aldrich. Microdroplets were generated by a standard oil-in-water dispersion procedure. Specifically, 15 µL corn oil doped with BODIPY was mixed with 985 µL diluted detergent and the mixture was shaken for 5 minutes until the oil was dispersed uniformly in the solvent. Other implementations for the droplet laser are readily understood by those skilled in the art.

Microwells served as receptacles for the oil droplets. For example, a 3×3 array of microwells with 50 µm in depth and 1 mm in diameter were fabricated in a biocompatible negative photoresist SU-8 on the surface of a 1"×1" glass slide using standard soft lithography. The mirrors were first cleaned by solvent ultrasonication (sonicated in acetone, ethanol, and de-ionized water sequentially) and oxygen plasma treatment. Then, they were dehydrated at 150° C. for 15 minutes right before a 50 µm thick SU-8 2025 (Micro-Chem Corp., USA) layer was spin-coated on the top of the mirrors. After soft-baking the SU-8-coated mirrors for 3 minutes at 65° C. and 8 minutes at 95° C., a contact lithography tool Karl Suss MA 45S was used to UV-expose the mirrors through a mask. The exposed mirrors were subsequently subjected to post-exposure baking at 65° C. for 1 minute and 95° C. for 6 minutes, followed by 8 minutes of development. After rinsing and drying, the microwell array was further hard baked at 150° C. for 10 minutes and treated with oxygen plasma to improve hydrophilicity. Before experimental measurement, the microdroplet solution was dripped into the microwells, which were then covered with a glass slide.

In the experimental setup, the glass capillary, which was used to simulate a blood vessel, was purchased from Thomas Scientific. It had a diameter of 700 µm and a wall thickness of 100 µm. To start with, the microdroplet solution was diluted 20× and mixed with human whole blood. Then the mixture was injected into the capillary, which was later sealed with UV curable epoxy (NOA 81). Finally, the capillary loaded with the sample was submerged 1 mm into ultrasound coupling gel.

A typical confocal setup was used to excite the oil droplet lasers and collect emission light. For example, a pulsed diode laser (pulse width: 2 ns, tunable repetition rate from 20 to 799 Hz) at 473 nm was loosely focused through a 20 mm focal length cylindrical lens to excite the oil microdroplets in microwells or capillaries. In the control experiments, a pulsed OPO laser (pulse width: 5 ns, repetition rate: 20 Hz) with 485 nm was applied to excite polystyrene beads doped with FITC. The pump intensity was controlled by a continuously variable neutral density filter. The emission light was collected through the same lens and sent to a spectrometer (Horiba iHR550, spectral resolution ~0.2 nm) for further analysis. For ultrasound modulation, focused ultrasound transducers with 500 kHz, 2.5 MHz, 10 MHz central frequency (500 kHz: H107, Sonic Concepts, Bothell, WA; 2.5 MHz: V307, Olympus Inc.; 10 MHz, V322, Olympus, Inc.) were driven by a function generator (Stanford Research Systems DS345) and a power amplifier (37 dB, custom design) to generate the desired ultrasound signals. A commercial calibrated hydrophone (ONDA HNC-1500) was used to measure the applied US pressure during the experiments at the focus of the ultrasound field.

Initially, the lasing spectra of the microdroplet laser were studied under a relatively low ultrasound pressure (10 kPa at 500 kHz). During the measurements, the microdroplet lasers were trapped and observed at the same position and with a constant pump energy density of 35 µJ/mm. To demonstrate the effect of ultrasound, the lasing spectra of the microdroplet laser were recorded before, during, and after continuous ultrasound exposure (FIG. 3A). Obviously, neither the lasing intensity nor the spectral peak position changed with the "low" ultrasound pressure, suggesting that small ultrasound disturbance does not affect droplet lasing behavior. In contrast, with a stronger ultrasound pressure (50 kPa at 500 kHz), significant enhancement (~20 times) in lasing intensity was observed when the ultrasound was turned on (FIG. 3B). In particular, strong lasing emission emerges from the rim of the droplet (see the inset of FIG. 3B). Furthermore, the enhancement is reversible, i.e., the lasing intensity falls back to the normal level when the ultrasound was turned off. During the ultrasound lasing enhancement, the lasing modes and their spectral positions remained the same (within the spectrometer resolution), indicating that the ultrasound, at the given pressure, did not cause any significant change in the shape and size of the oil microdroplets. In FIG. 2C, the microdroplet lasing threshold was investigated with and without the exposure to the ultrasound pressure. It was found that the lasing threshold was reduced from 19 µJ/mm$^2$ to 11 µJ/mm$^2$ with a 10× increase in the intensity efficiency (the slope of the laser output) when the microdroplet was exposed to the US pressure of 50 kPa.

The relationship between the microdroplet lasing intensity and the US frequencies was also investigated with results shown in FIG. 4. All the lasing spectra were acquired with the same integration time of 1 s under the fixed pump energy density of 40 µJ/mm. Focused ultrasound transducers worked at various frequencies (500 kHz, 2.5 MHz, and 10 MHz, respectively) were utilized to generate continuous ultrasound that was applied to microdroplet lasers. A pressure threshold around 30 kPa was noted for all the three ultrasound frequencies. Below the pressure threshold, no enhancement in laser intensity was observed (see also FIG. 3A). While above the pressure threshold, the enhancement became linearly proportional to the ultrasound pressure. In addition, it seems that the ultrasound with lower frequency led to higher enhancement, as demonstrated by the steeper slope above the pressure threshold in FIG. 4A compared to those in FIGS. 4B and 4C.

The phenomena observed above, including the lasing intensity enhancement and the ultrasound threshold behavior, can be understood in the framework of directional emission from an asymmetric resonator cavity (ARC). In the absence of ultrasound, the droplet maintains a nearly perfect spherical shape and the lasing output is weak and isotropic. In the focused ultrasound field, the droplet is steadily deformed to become ellipsoidal by the second-order acoustic radiation force. With a relatively low acoustic pressure (and hence a low acoustic radiation force), the deformation of the droplet is insignificant, and the weak, isotropic lasing emission is preserved. With the increased acoustic pressure (and hence the increased acoustic radiation force), the smoothly deformed droplet breaks the spherical symmetry of the WGM cavity and the ray dynamics becomes partially chaotic, leading to high power directional laser emission (or chaos-assisted tunneling). Due to the relatively large refractive index contrast between those WGM cavities and the surrounding media, a relatively large deformation threshold (e.g., 5%) is needed to have directional emission. However, in this experiment, the refractive index contrast between the oil and water is only 1.1, and therefore, directional emission can be achieved with a smaller deformation. Based on the ultrasound threshold in FIG. 4 and the theoretical analysis in FIG. 2B, it was estimated that even only 0.1% deformation is sufficient to cause the directional emission. For biomedical applications, a low deformation threshold is desirable since low ultrasound intensity is needed to modulate droplet lasers.

To further confirm the mechanism of the enhanced lasing emission described above, two groups of control experiments we conducted. First, the fluorescence intensity from the microdroplet of the similar size (~50 µm in diameter) doped with the same concentration of BODIPY was studied. No difference in fluorescence intensity was observed between the strong ultrasound pressure (50 kPa at 500 kHz) and no ultrasound pressure (0 kPa), indicating that ultrasound has no effect on the fluorescence efficiency of the dye molecules. Second, the same ultrasound enhanced lasing emission was performed on 10 µm diameter polystyrene beads doped with fluorescence dye, FITC. When pumped at 485 nm, lasing emission from the beads was clearly observed. However, even in the presence of a strong ultrasound pressure (50 kPa at 500 kHz), the lasing intensity remains virtually unchanged due to the high Young's modulus (3 GPa) of polystyrene and hence the negligible bead deformation.

FIG. 5A shows the capability to non-invasively modulate the microdroplet laser emission by changing the ultrasound intensity. In particular, a 500 kHz focused ultrasound transducer was used to produce multiple cycles of pressure (0→2 kPa→60 kPa→12 kPa→0). Every time when a strong ultrasoundS pressure of 60 kPa was applied, significant lasing enhancement of 4-6-fold could be observed compared to the laser emission at ultrasound pressure of 0 and 12 kPa. In addition to the ultrasound intensity, the laser emission can also be controlled by the ultrasound duty cycle. FIG. 5B presents the laser emission intensity with 0%, 24%, and 48% duty cycle under the same ultrasound pressure (50 kPa at 500 kHz). With the increased duty cycle, the lasing intensity increases linearly. Finally, it was demonstrated that the laser emission enhancement by short ultrasound bursts. A series of ultrasound bursts (500 kHz, 60 kPa, 60 ms burst duration) was utilized to trigger the enhanced microdroplet laser emission with a repetition frequency of 0.5 Hz. The laser emission was collected with an exposure time of 0.5 s. From the synchronized ultrasound pressure and laser intensity curves in FIG. 5C, it can be seen that the lasing intensity follows the ultrasound burst at the same repetition frequency.

The ability to temporally modulate the laser emission is the key to significantly improving the SNR. This becomes even more critical when applying the microdroplet laser for sensing and imaging in deep tissues. First, a series of short ultrasound bursts (500 kHz, 60 kPa, 30 ms burst duration) with a repetition frequency of 8 Hz was applied to the microdroplet laser. A CCD camera was used to continuously record the laser output intensity. The pump laser was set at 40 Hz with an energy density of 50 µJ/mm$^2$ to match the image sampling rate of 40 fps. FIG. 6A presents the raw intensity curve as a function of time extracted from the recorded images. FIG. 6B shows the frequency domain analysis of the signal in FIG. 6A with a bandpass (6-10 Hz) FFT digital filter. A distinct 8 Hz component in the frequency spectrum is observed corresponding to the 8 Hz US bursts. Then, a series of short ultrasound bursts (500 kHz, 60 kPa, 15 ms burst duration) with a repetition frequency of 20 Hz was applied to the microdroplet laser. Similarly, the pump laser was set at 80 Hz with an energy density of 50 µJ/mm$^2$ to match the image sampling rate of 80 fps. FIG. 6C presents the raw intensity curve as a function of time extracted from the recorded images. By applying a bandpass FFT digital filter (15-25 Hz), a 20 Hz modulated frequency component in laser output can be seen in FIG. 6D with an SNR of approximately 30.

To demonstrate the potential applications of the ultrasound modulated droplet laser to biological tissues, in FIG. 7A a glass capillary embedded 1 mm in an optical scattering gel is used to simulate a blood vessel. The oil droplets were mixed with human whole blood and injected into the capillary. Initially, a continuous US pressure (40 kPa at 500 kHz) was focused on the blood vessel phantom, and enhanced lasing intensity was observed. The enhancement was reversible after turning the ultrasound radiation off (FIG. 7B). This result verifies that the ultrasound lasing enhancement persists even when the droplets are surrounded by whole blood. Next, a series of short ultrasound bursts (500 kHz, 60 kPa, 60 ms burst duration) at 4 Hz repetition frequency was used to modulate the droplet laser. The lasing emission was collected by a CCD camera with 20 fps, as the result shown in FIG. 7C. After applying a bandpass FFT digital filter of 2-6 Hz, the modulation component at 4 Hz can be easily extracted with a high SNR of 25, as shown in FIG. 7C.

This disclosure demonstrated acoustic modulated lasers utilizing, for example biocompatible microdroplet lasers and low intensity focused ultrasound transducers. By conjugating the droplet lasers with targeted cells, imaging and tracking of cellular dynamics can be achieved in-vivo in subsurface tissues. Without targeting any biological entities, the droplet lasers injected into the circulatory system such as blood vessels can also work as a blood pool agent to achieve high-resolution laser emission imaging of the vasculature, as well as flow dynamics in biological samples. Besides potential contributions to biology and medicine, the method described in this disclosure provides a new platform to tune the cavity shape and size remotely, non-invasively, and continuously by ultrasound, which is important for fundamental research and the development of novel photonic devices.

The techniques described herein or portions thereof may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

Some portions of the above description present the techniques described herein in terms of algorithms and symbolic representations of operations on information. These algorithmic descriptions and representations are the means used by those skilled in the data processing arts to most effectively convey the substance of their work to others skilled in the art. These operations, while described functionally or logically, are understood to be implemented by computer programs. Furthermore, it has also proven convenient at times to refer to these arrangements of operations as modules or by functional names, without loss of generality.

Unless specifically stated otherwise as apparent from the above discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

Certain aspects of the described techniques include process steps and instructions described herein in the form of an algorithm. It should be noted that the described process steps and instructions could be embodied in software, firmware or hardware, and when embodied in software, could be downloaded to reside on and be operated from different platforms used by real time network operating systems.

The present disclosure also relates to an apparatus for performing the operations herein. This apparatus may be specially constructed for the required purposes, or it may comprise a computer selectively activated or reconfigured by a computer program stored on a computer readable medium that can be accessed by the computer. Such a computer program may be stored in a tangible computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The algorithms and operations presented herein are not inherently related to any particular computer or other apparatus. Various systems may also be used with programs in accordance with the teachings herein, or it may prove convenient to construct more specialized apparatuses to perform the required method steps. The required structure for a variety of these systems will be apparent to those of skill in the art, along with equivalent variations. In addition, the present disclosure is not described with reference to any particular programming language. It is appreciated that a variety of programming languages may be used to implement the teachings of the present disclosure as described herein.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An imaging system, comprising:
a laser that outputs a laser beam, wherein largest dimension of the laser is less than a millimeter;
a modulating source that generates acoustic radiation and is configured to modulate the laser beam with the acoustic radiation;
an optical detector configured to detect the modulated laser beam from the laser;
and a controller interfaced with the modulating source and the optical detector,
wherein the modulating source is configured to modulate the laser beam by changing the shape of the cavity of the laser with the acoustic radiation incident thereon.

2. The imaging system of claim 1 wherein the laser is one of a microsphere laser, a ring resonator laser, a distributed feedback laser, a nanowire laser, a plasmonic laser or a photonic crystal laser.

3. The imaging system of claim 1 wherein the laser is embedded into at least one of a cell, tissue or blood vessel of a subject.

4. The imaging system of claim 1 wherein the modulating source is configured to modulate amplitude of the laser beam.

5. The imaging system of claim 1 wherein the modulating source is configured to focus the acoustic radiation and to report position of the focused acoustic radiation to the controller.

6. The imaging system of claim 1 wherein the acoustic radiation is further defined as ultrasound radiation.

7. The imaging system of claim 1 wherein the optical detector is further defined as charge-coupled device.

8. An imaging system, comprising:
a microsphere laser that outputs a laser beam;
a modulating source that generates acoustic radiation and is configured to modulate the laser beam of the microsphere laser by deforming the cavity of the microsphere laser with the acoustic radiation incident thereon with the acoustic radiation;
an optical detector configured to detect the modulated laser beam from the microsphere laser; and
a controller interfaced with the modulating source and the optical detector.

9. The imaging system of claim 8 wherein the microsphere laser is comprised of a gain medium, an optical feedback component and an external pump source, such that the largest dimension of the gain medium and the optical feedback component is less than a millimeter.

10. The imaging system of claim 8 wherein the microsphere laser includes oil doped with dyes.

11. The imaging system of claim 8 wherein the microsphere laser is embedded into at least one of a cell, tissue or blood vessel of a subject.

12. The imaging system of claim 8 wherein the modulating source is configured to modulate amplitude of the laser beam.

13. The imaging system of claim 8 wherein the modulating source is configured to focus the acoustic radiation and to report position of the focused acoustic radiation to the controller.

14. The imaging system of claim 8 wherein the acoustic radiation is further defined as ultrasound radiation.

15. The imaging system of claim 8 wherein the optical detector is further defined as charge-coupled device.

\* \* \* \* \*

UNITED STATES PATENT AND TRADEMARK OFFICE
CERTIFICATE OF CORRECTION

| | | |
|---|---|---|
| PATENT NO. | : 12,000,782 B2 | Page 1 of 1 |
| APPLICATION NO. | : 17/421809 | |
| DATED | : June 4, 2024 | |
| INVENTOR(S) | : Xudong Fan et al. | |

It is certified that error appears in the above-identified patent and that said Letters Patent is hereby corrected as shown below:

On the Title Page

At page 2, Column 1, (57) Abstract, Line number 1, after "imaging", insert --.--.

Signed and Sealed this
Fourth Day of February, 2025

Coke Morgan Stewart
*Acting Director of the United States Patent and Trademark Office*